Figure 1:
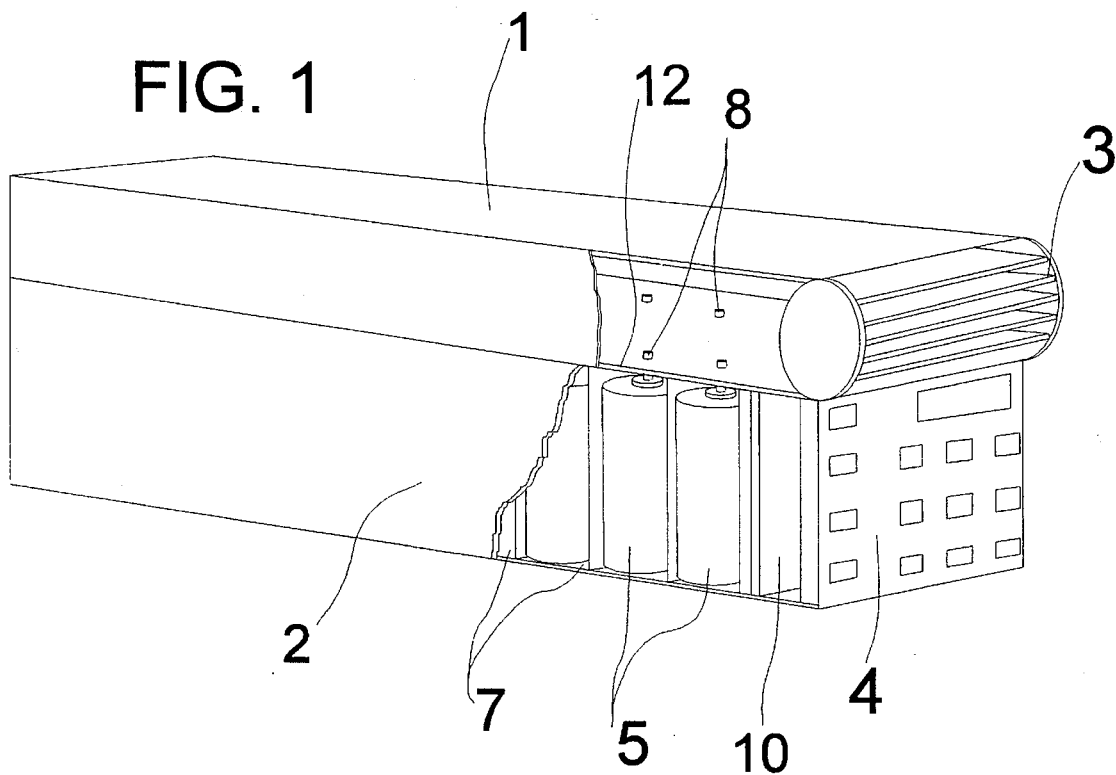
Figure 2:
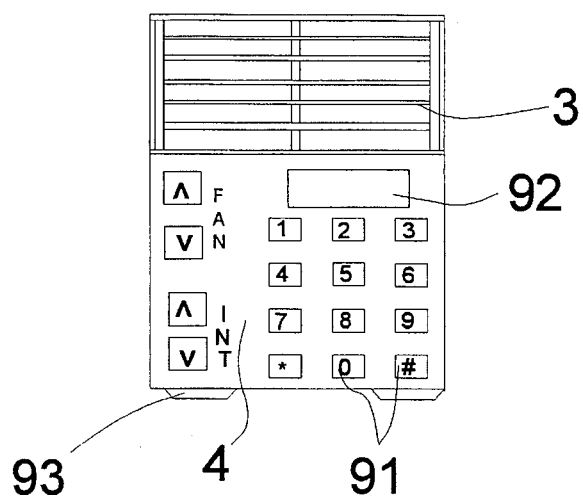
Figure 3:
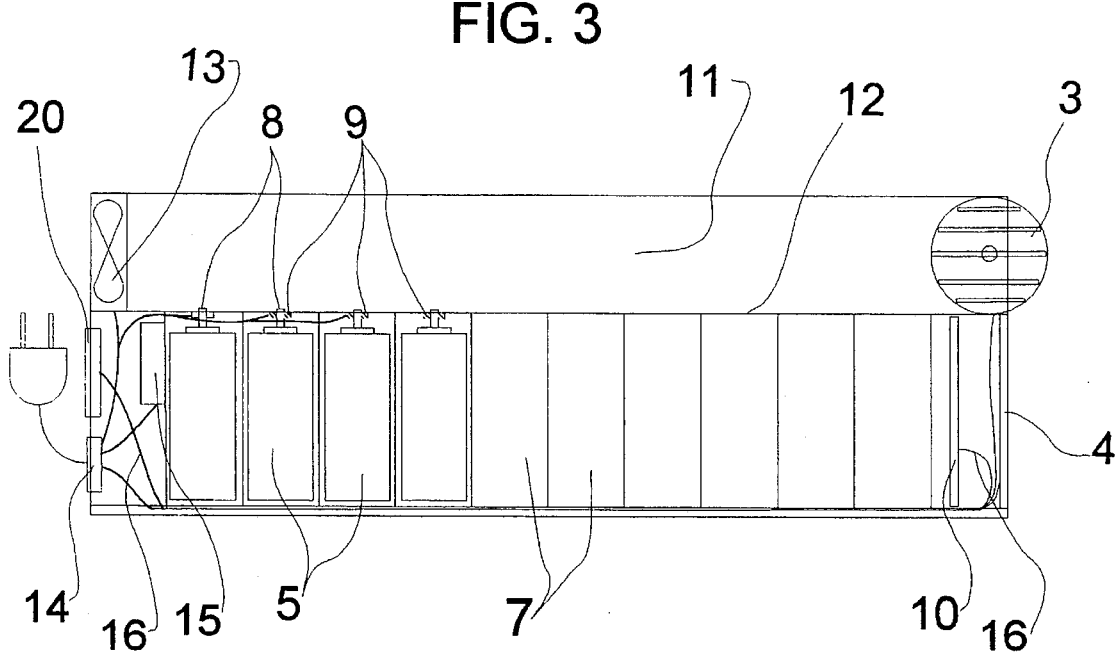
Figure 5:
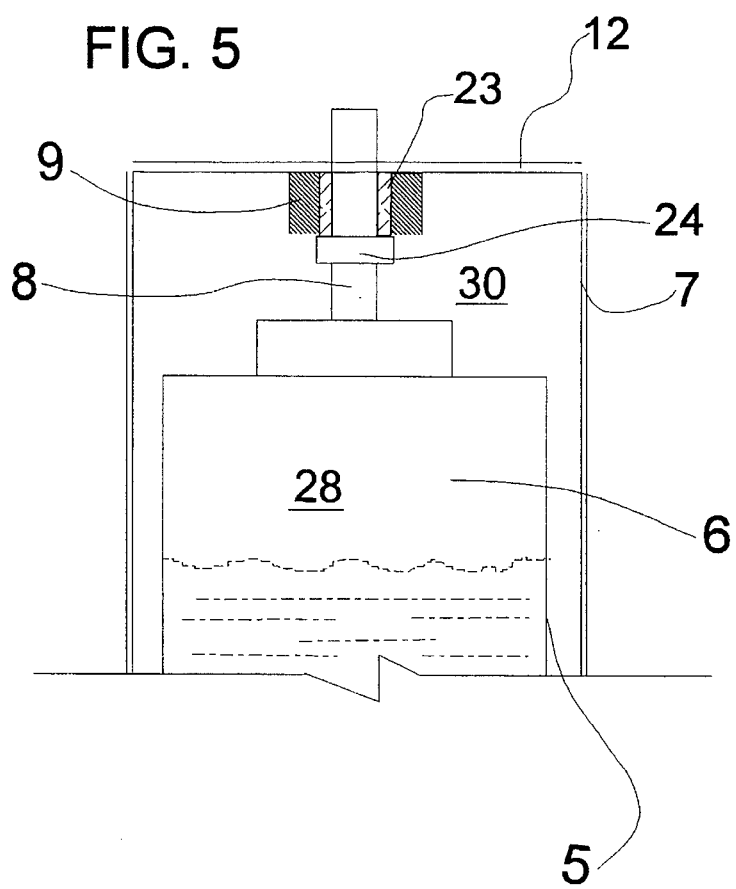
Figure 4:
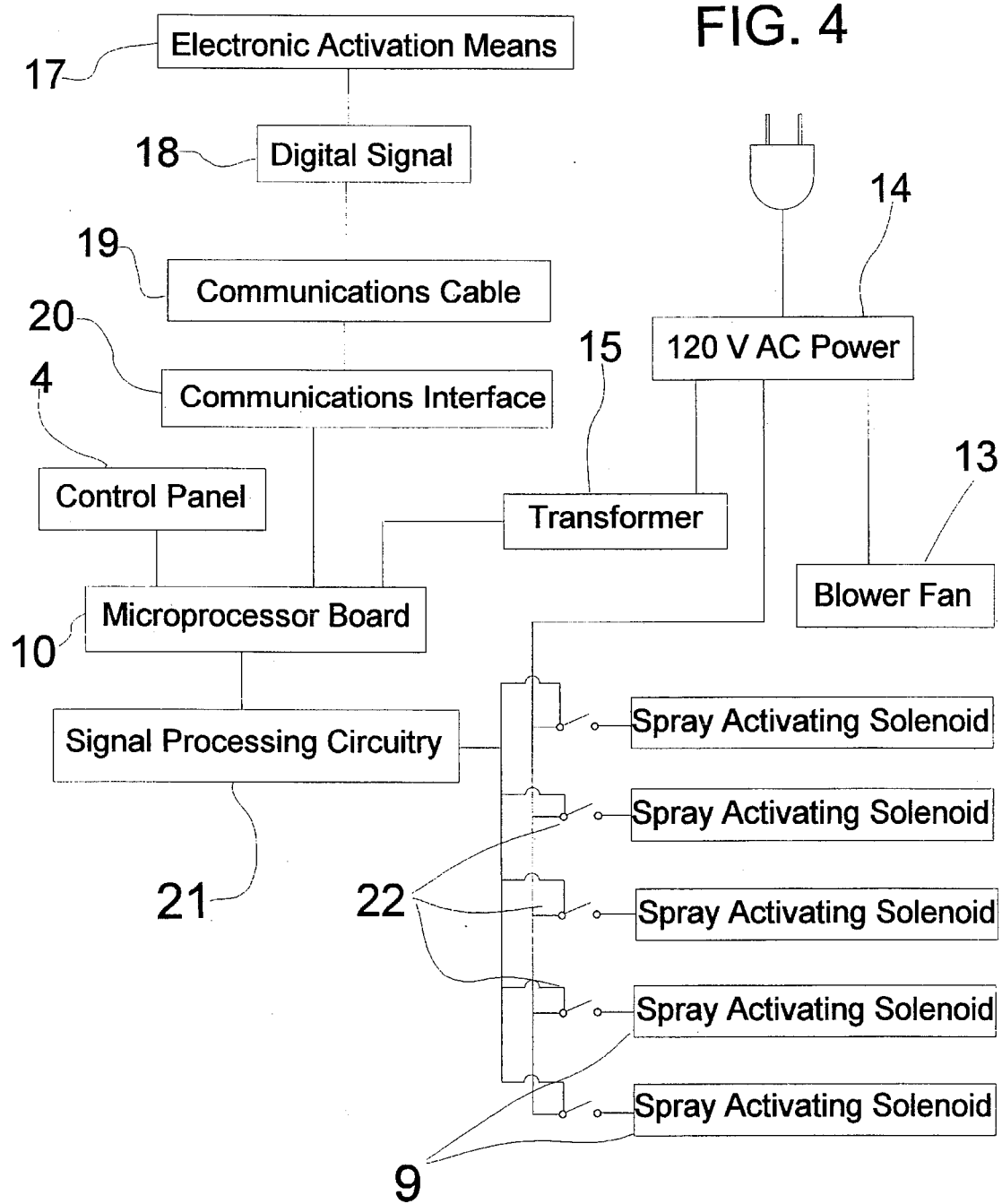

United States Patent [19]
Watkins

[11] Patent Number: 5,591,409
[45] Date of Patent: Jan. 7, 1997

[54] PROVIDING AROMAS

[76] Inventor: Carl J. Watkins, 2055 W. 25th Ave., Eugene, Oreg. 97405

[21] Appl. No.: 515,275

[22] Filed: Aug. 15, 1995

[51] Int. Cl.$^6$ ............................................. G05D 7/00
[52] U.S. Cl. .................... 422/110; 422/1; 422/4; 422/5; 422/108; 422/116; 422/119; 422/120; 422/123; 422/124; 422/125
[58] Field of Search ........................... 422/1, 4, 5, 120, 422/123, 124, 125, 119, 108, 110, 116

[56] References Cited

U.S. PATENT DOCUMENTS

| | | | |
|---|---|---|---|
| 2,686,944 | 8/1954 | Gubelin | 422/124 |
| 3,804,592 | 4/1974 | Garbe | 422/124 |
| 4,556,539 | 12/1985 | Spector | 422/125 |
| 4,952,024 | 8/1990 | Gale | 350/143 |
| 5,023,020 | 6/1991 | Machida et al. | 422/124 X |
| 5,105,133 | 4/1992 | Yang | 422/124 X |
| 5,171,485 | 12/1992 | Ryan | 422/124 X |
| 5,297,988 | 3/1994 | Nishino et al. | 422/124 X |
| 5,318,503 | 6/1994 | Lord | 600/27 |

*Primary Examiner*—Robert J. Warden
*Assistant Examiner*—Krisanne M. Thornton
*Attorney, Agent, or Firm*—Philip M. Dunson; Philip J. Pollick

[57] ABSTRACT

Apparatus and methods for use with electronic activation means such as work or entertainment systems introduce precisely controlled amounts of aromatic chemicals, using metered spray technology, into the immediate vicinity of the operator. Control is provided by microprocessor circuitry so that aromas may be used at appropriate times and intensities by computer or entertainment sources. Multiple removable spray containers may generate numerous aromatic enhancements to a wide variety of applications.

15 Claims, 8 Drawing Sheets

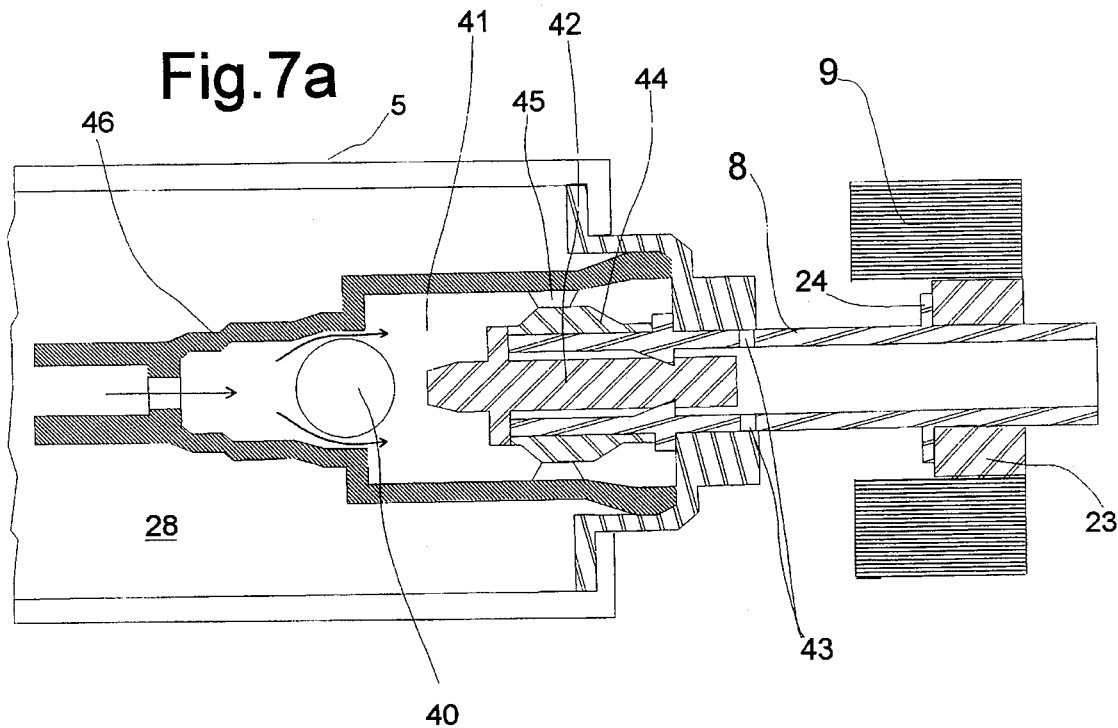
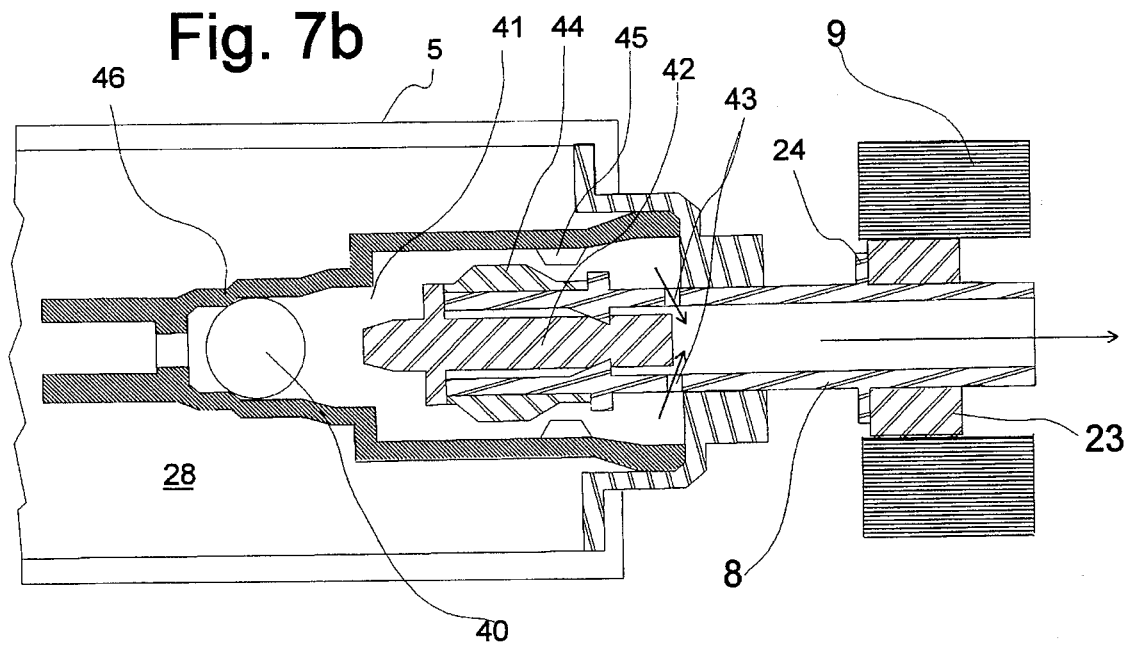

71  72  73

81  82  83
       84  85

PROVIDING AROMAS

This invention relates to apparatus and methods for providing aroma emitting material to predetermined regions from time to time. It has to do particularly with such apparatus and methods that typically include in combination the steps of, and means for, providing signals at selected times when an aroma is to be emitted, containing an aroma producing material in a selected confining region except when actuated to release some of the material therefrom, and releasing a controlled quantity of the material to the adjacent atmosphere in response to electronic or optical signals from an entertainment device and/or digital data processing means.

BACKGROUND

It is known to spread odors in auditoriums or viewing rooms through various techniques, including heating and spraying methods, with the purpose of enhancing cinematic, television, or other video entertainment.

It is also known to employ cartridges or other containers of odorous substances which, when selected by a pre-programmed method spread odors throughout the room.

It is also known to employ elaborate venting systems to evacuate odors from the room so that new odors can be introduced.

However, it is not known to precisely control the amount of odor causing chemicals introduced into the atmosphere of the room, particularly in a relatively confined area.

It is not difficult to introduce scents into a room at predetermined times, and later to remove them with air circulating means. The main difficulty is in managing the intensity of the aromas, as well as the timing and duration of the scent, in conjunction with the other entertainment sources, for individual viewers.

Previous technologies have offered numerous means of introducing chemical aromas into a room using methods that produce a wide range of intensity and duration. These means have typically employed imprecise techniques, such as opening and closing a hooded container as in McCarthy U.S. Pat. No. 4,603,030, spraying an approximate quantity of a chemical with an easily contaminated vaporizer as in Laube U.S. Pat. No. 2,905,049, or heating a liquid permeated material or compound as in Lee U.S. Pat. No. 5,398,070.

These methods usually contemplated disbursing relatively large quantities of scent into auditoriums or rooms, wherein numerous individuals would be affected by the introduction of aromatic chemicals. These previous techniques allowed for uncontrolled intensities of aroma, with the additional drawbacks that they were slow in delivering the scent, and scents continued to be generated even after they were no longer activated or intended.

The introduction of microcomputers as personal activity centers has changed the orientation of entertainment, employment, and avocations. It is therefore desirable to have a programmable aroma generating mechanism oriented toward its use by an individual sitting at a desk using a microcomputer. Such a circumstance requires a much more precise method of generating and evacuating chemical aromas.

DISCLOSURE

This can be achieved by means of typical methods according to the present invention, which are characterized by a closely controlled spray technology capable of delivering very small and precise increments of aroma carrying chemicals. These may be sprayed directly at the user, but in the preferred embodiments of this invention, the scent is sprayed into a directionally controlled disbursement means.

The mechanism typically is constructed with materials which are minimally permeable by aromatic chemicals, thereby reducing the persistence of aroma after its cessation is desired. Suitable such materials include polytetrafluoroethylene and other somewhat similar materials having non-stick surfaces. Such a mechanism also makes it possible to obtain a blending of multiple scents in precisely defined combinations for additional impact.

To achieve the desired aromatic effect, typically a spraying means delivers a controlled quantity of aromatic vapors into a chamber through which air is continually moving. A fan or blower mechanism brings air in, and pushes the aroma laden air out through a portal directed at the nasal olfactory senses of the user. On discontinuance of the spray, the continually moving air removes the aromatic vapors from the chamber, clearing it for the next generation of scent. The unscented air moves on to the nose of the user, thereby clearing the user's olfactory sensors in anticipation of the introduction of the next aroma.

The mechanism for spraying the scents can be of several varieties, but the essential capability of these mechanisms is their ability to project a controlled small quantity of aromatic vapors. In a typical version depicted in the drawings of this patent, a metered aerosol projecting means in pressurized containers is shown, as well as a metered pump spray mechanism and an electrothermal jetting technology which may be used as well. In fact, a combination of these may be used as dictated by the requirements of the various scent conveying chemical means. The spray activation method in a typical embodiment uses an electronically activated solenoid, but numerous other electro-mechanical means may be employed without departing from the scope of this invention.

An added benefit of using small sized metered spray container technology is that a large number of scents may be contained in a desktop mechanism, further enhancing the individualistic focus of this invention, and eliminating the need to manually exchange scent carrying means, in order to expand the number of available scents.

Controlled or metered spraying techniques offer the distinct advantage over previous methods of generating aromas by effecting a closing and sealing of the chemical container. This provides a means for discontinuing the scent, minimizing further escape of the aroma. Additionally, metered spray techniques solve consistency problems inherent in non-metered spray mechanisms. Non-metered mechanisms often emit exceptionally large droplets when activated, or they may emit no droplets at all, depending on the length of time from one activation to the next.

The use of a solenoid to automatically activate the spray of aromatic chemical is an improvement over Stern U.S. Pat. No. 2,540,144 where a solenoid is used as the means to open and close a pressurized chemical reservoir. In that case, an unmeasurable mechanical regulatory valve governs the level of chemical emissions, and a solenoid is used to hold open the exit tube for the pressurized chemical. No attempt is made to control the amount of chemical emitted in any quantifiable way. Westenholz U.S. Pat. No. 3,795,438 shows a similar mechanical means of opening an aperture to allow the escape of aromatic chemicals in minimally controlled amounts.

The ability to control the amount and duration of emission of aromatic chemicals is an improvement over Spector U.S.

Pat. No. 4,629,604 where heating means is used to volatilize chemical laden pads in predetermined sequences but does not recognize the tendency of aromas to persist in volatilization, or to permeate surrounding air without augmentation by heat. Further, Spector relies on gravity to circulate aromas, which is much too slow and ineffective for the applications of the present invention.

It is also contemplated that the means for delivering the aromatic spray to the olfactory sensors of the user may be augmented with more elaborate attachments, such as a tube and face mask, as may be desired for use in games or virtual reality applications. Another variation is a tube with an opening on the end, which is attachable to a headset microphone located in close proximity to the users nose.

The control of this mechanism typically is through the use of microprocessor circuitry, which controls the timing and frequency of spray. The control circuitry typically is linked to programmable electronic activation means through the use of industry standard communications means. A universally available software control format is provided so that many varied applications may be developed using the capabilities of this invention.

Figure 6A:
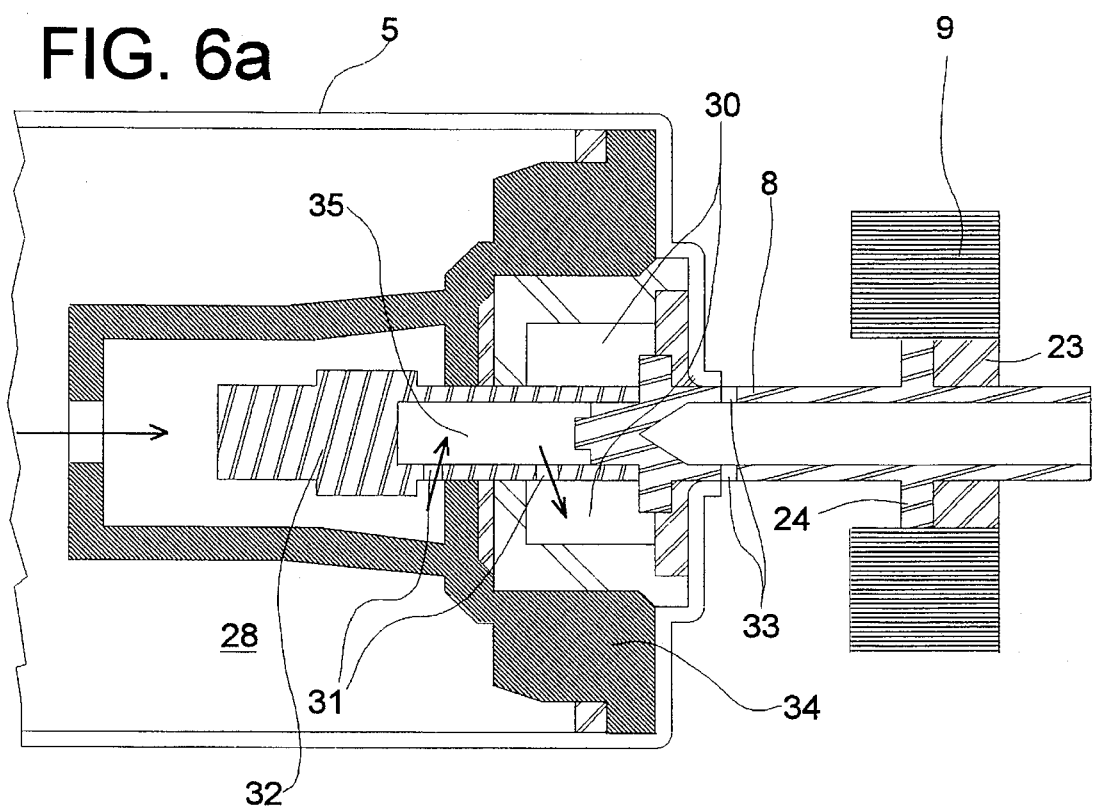
Figure 6B:
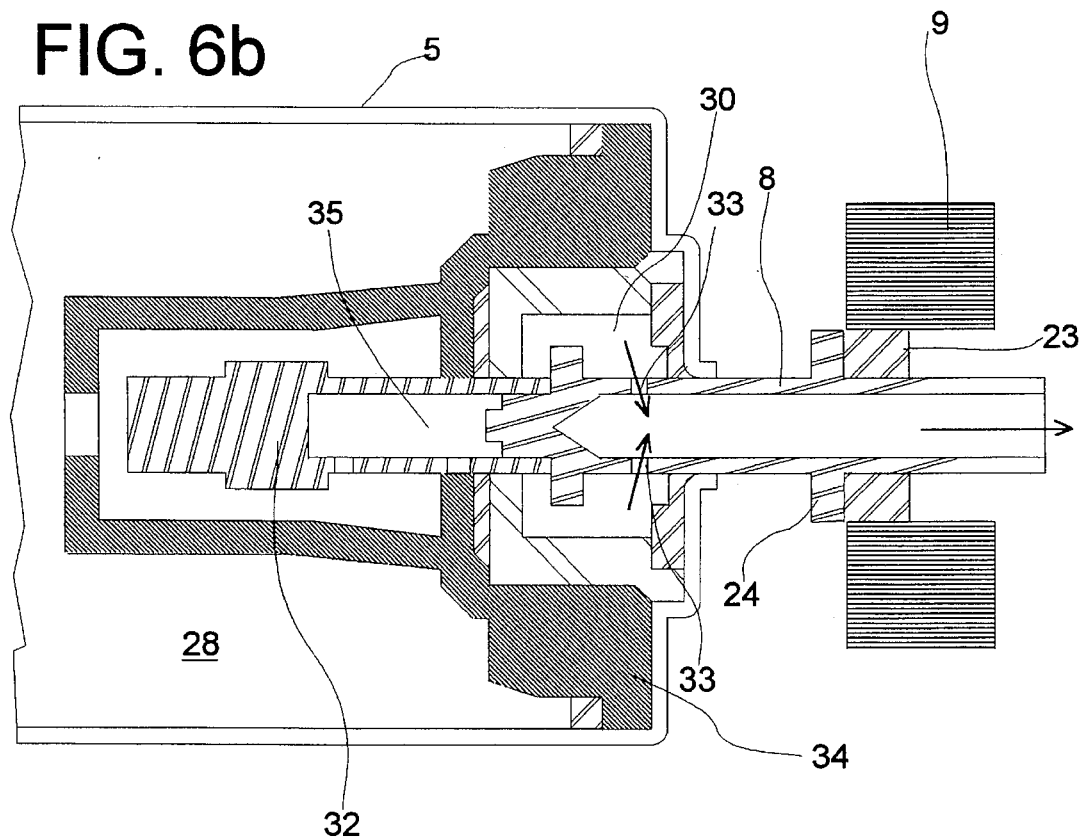

The fan that moves air through a spraying chamber and then out the directional control typically is adjustable in speed, so that wherever the mechanism is placed, it can be adjusted to a comfortable level. Intensity of aroma is adjustable, and a control panel provides an additional means to adjust fan speed and intensity of typical aroma generators of this invention. Multiple enclosures can be used in combination so that a large number of scents can be generated without having to replace aromatic scent containers.

Typical apparatus of this invention for generating multiple aromas in precise amounts in conjunction with a programmable means can have many applications. It can serve to create a productive atmosphere through the augmentation of aromatherapy techniques while the users work at their desks. It can serve to add impact to games and multimedia presentations. It can be used as an aid to educational programs, as scent has been shown to enhance memorization and recall. This invention is designed to fit into the desktop area with minimal rearrangement.

This invention can have many applications associated with microcomputers, video, television, and cinema. Communication interfaces and programmable means typically are provided so that these applications may take advantage of this invention, and it can easily be modified so as to be controlled remotely through wave transmission means.

BRIEF DESCRIPTION OF THE DRAWINGS

FIG. 1 is an isometric view of a typical mechanism according to this invention.

FIG. 2 is a frontal perspective view of the device.

FIG. 3 is a schematic diagram of typical electronic components.

FIG. 4 is a side view of the mechanism with the side panel removed.

FIG. 5 is a detail sectional view of typical solenoid spray activation means.

FIGS. *6a* & *6b* are detail sectional views of a typical aerosol metered spray means.

FIGS. *7a* and *7b* are detail sectional views of a typical pump metered spray mechanism.

FIGS. *8a* and *8b* are detail sectional views of an alternative solenoid activation means.

FIG. 9 is a sectional view of a typical thermal jet metered spray mechanism.

FIG. 10 is an isometric view of an alternatively oriented mechanism.

FIG. 11 is an isometric view of a typical face mask delivery attachment.

FIG. 12 is an isometric view of a typical microphone delivery attachment.

CARRYING OUT THE INVENTION

In a typical embodiment of the device according to the invention as shown in FIGS. 1, 2, 3 and 4, there is a structural enclosure 1 having removable side panels 2 on either side, a directional vent control 3, and a control panel 4. Removable containers 5 of aromatic chemicals 6 are placed into individual chambers 7 in linear arrays of two or more such that the spray nozzle 8 fits into the spray activating solenoid 9. Electrical circuitry controlled by a microprocessor board 10 initiates the action of the spray activator 9 discharging the aromatic chemical into the venting chamber 11.

An air blowing fan 13 causes air to be taken in through the back of the enclosure of this invention, where it is caused to flow along the nozzles 8 of the spray containers which protrude through holes in the base 12 of the venting chamber 11. The fan 13 runs continuously to move the aromatic vapor out of the venting chamber 11 where, upon its exit, it is guided by the directional vent control 3 toward the nose of the user of this invention. Power is supplied to the electronics of this invention through external power source 14 which connects to a transformer 15, the spray activating solenoids 9 and the Fan 13. Wiring 16 connects the transformed power to the circuit board 10 and the control panel 4.

The control panel 4 shown in FIG. 2 consists of input buttons 91 for designating scents, controlling fan speed and intensity aromatic chemical emission, programming the timing of the emissions. A light emitting diode display 92 assists in programming the generation of scents without the use of a microcomputer or other external programming input means. Rubber supports 93 attached to the underside of the enclosure of this invention provide friction to help keep in position and provide a measure of stability.

FIG. 4 shows the sequence of operation of this invention where an electronic activation means 17, such as a computer, transmits a digital signal 18 through a communications cable 19 connected to the communication interface 20. This digital signal 18 is interpreted by the signal processing circuitry 21 of the microprocessor board 10 and appropriate instructions are relayed to switches 22 controlling the spray activating solenoids 9.

FIG. 5 shows the spray activator 9 being a solenoid type device with a movable hollow sleeve 23 which, upon the application of an electrical charge, moves to push against a nozzle collar 24 causing the aromatic chemical 6 to be propelled into the venting chamber 11 through holes in the chamber base 12.

FIG. *6a* shows the means by which the electrical charge applied to the solenoid 9 activates an aerosol spray means (Valve 356, Tenax Corp, Apex, N.C.) attached to the container 5 containing aromatic chemical 6. FIG. *6a* indicates with arrows that during normal storage conditions, the chemical 6 will flow into the metering chamber 30 through holes 31 in the sides of the core 32 passing through filling chamber 35 capturing a measured amount of chemical 6 in the metering chamber 30.

FIG. 6b shows how the lateral movement of the solenoid sleeve 23 applies pressure to the nozzle collar 24 activating the spray mechanism and causing a measured amount of chemical to escape through holes 33 in the sides of the hollow nozzle 8 indicated by arrows. While in this position, filling holes 31 are prevented from allowing flow into the metering chamber 30 by blockage by the body 34 of valve mechanism. When the electrical charge on the solenoid activation mechanism 9 is terminated, the core 32 and nozzle 8 return to the position as shown in FIG. 6a allowing the metering chamber 30 to be re-filled through holes 31.

FIGS. 7a and 7b show a similar application of a solenoid used to activate a metered pump spray valve means (Valve C653-001, Tenax Corp, Apex, N.C.). In FIG. 7a a ball stopper 40 allows the metering chamber 41 to fill with aromatic chemical indicated by an arrow by means of a vacuum created when the pump mechanism returns to its normal position after activation. In FIG. 7b the solenoid activator sleeve 23 pushes the nozzle collar 24 causing the nozzle 8 and core 42 to move into the metering chamber 41 creating pressure which causes the valve 40 to press against the shoulder 46 and causes the aromatic chemical to be forced through a gap between a piston 44 and a ring 45. The chemical is then forced out of holes 43 exiting the nozzle 8 as indicated by arrows.

Figure 8A:
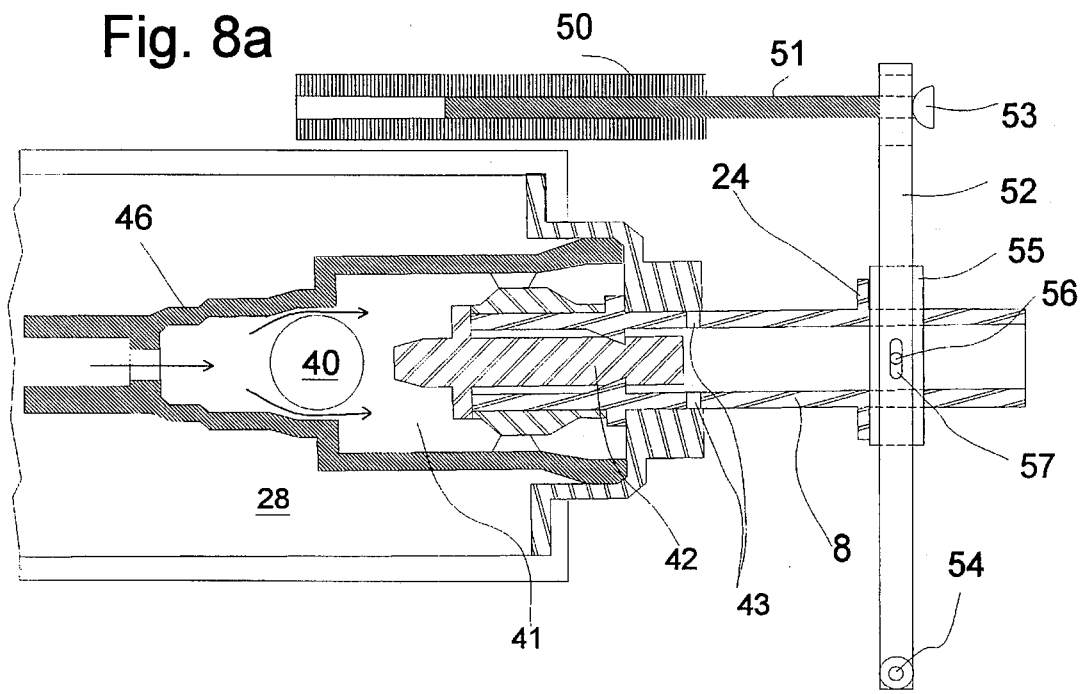
Figure 8B:
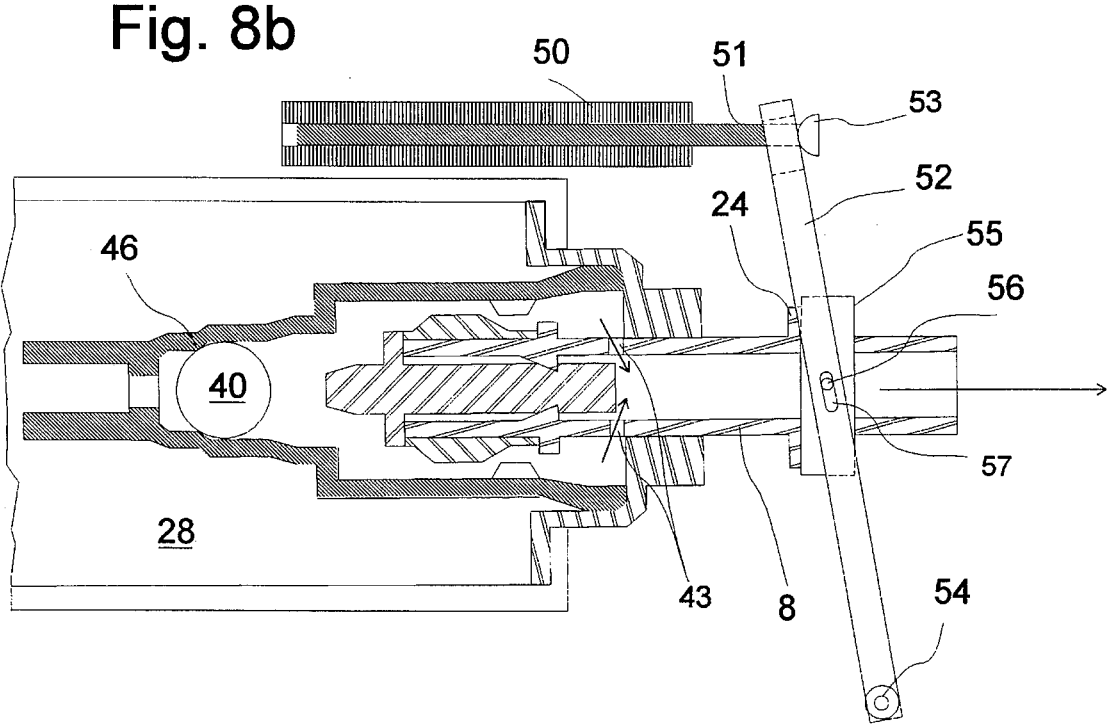

FIGS. 8a and 8b show an alternative means of activating the metered spray means similar to the one shown in FIGS. 7a and 7b by using a solenoid 50 with movable extension 51 attached to lever 52 by flange 53 which through linear movement pulls lever 52 which is attached at hinge 54. When the solenoid 50 receives an electrical charge, extension 51 moves to apply force to the activator cap 55 through attachment pins 56 which slide within slots 57 on both sides of the lever 52. This pressure moves the nozzle 8 and core 42 similarly to the activation means in FIGS. 7a and 7b.

Figure 9:
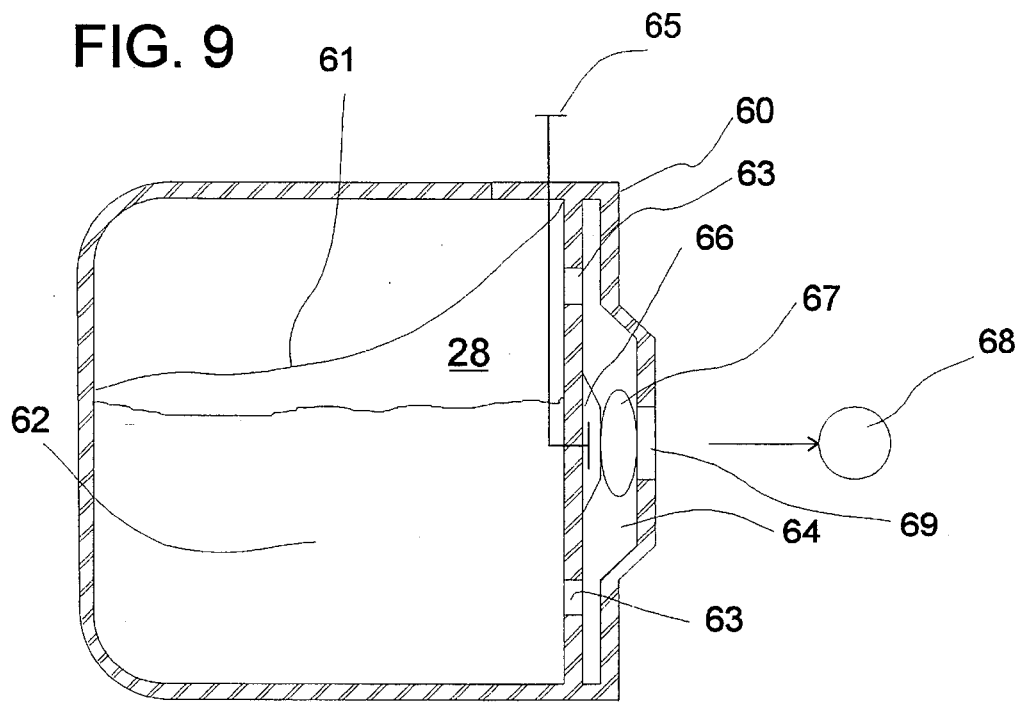

FIG. 9 shows an alternative method of spraying aromatic chemicals into the venting chamber 11 using a thermal jet spray mechanism 60 (HP 51604A, Hewlett Packard Co. Menlo Park, Calif.) wherein a flexible bladder 61 filled with aromatic chemical provides by capillary action said chemical 62 through portals 63 into chamber 64. An electrical charge 65 applied to heating element 66 causes a vapor bubble 67 to form, pushing a droplet 68 through escape portal 69.

Figure 10:
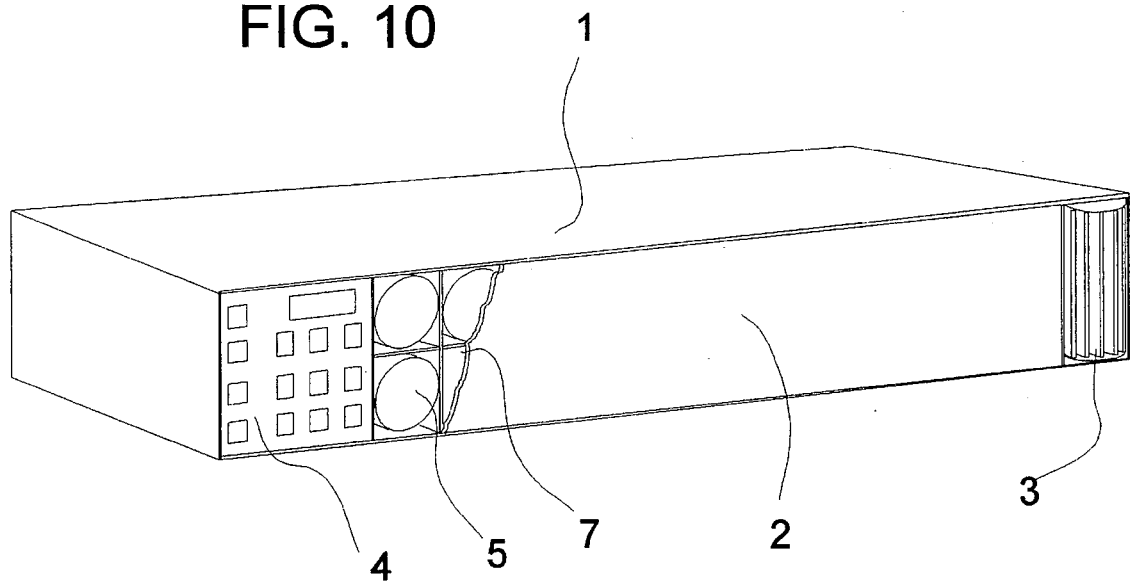

FIG. 10 shows an alternative configuration for orientation of this invention using horizontally stacked containers.

Figure 11:
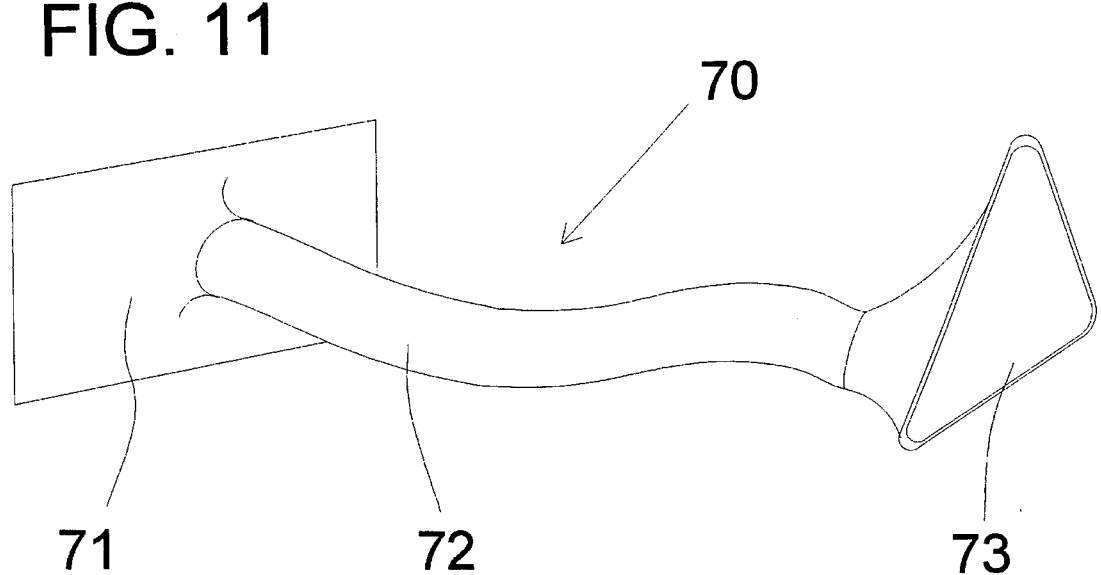

FIG. 11 shows an attachment 70 comprising a cover manifold 71, a transmission tube 72 and a face or nose mask 73 to be used to deliver aromas to the user's olfactory sensors in an even more controlled and direct manner.

Figure 12:
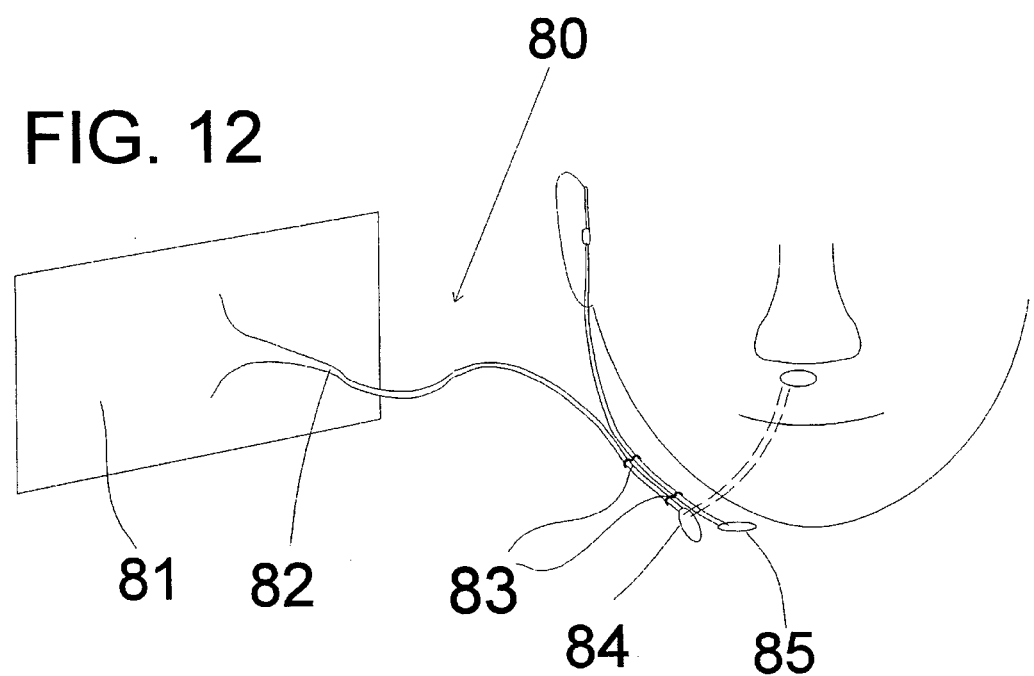

FIG. 12 shows an alternative attachment 80 comprising a cover manifold 81, a transmission tube 82 attachment means 83 and emission port 84. This variation is intended to be used with a headset 85 and microphone extension, as shown, or with its own head mounted support means, which may include a flexible or pivoting means for moving the emission port 84 closer to the nose.

To summarize, typical apparatus according to the present invention for providing aroma emitting material 6 to a predetermined region from time to time comprises means 4,10,14–22 for providing signals at selected times when an aroma is to be emitted, means 5 for containing an aroma producing material 6 and confining the material 6 therein except when actuated to release some of the material 6 therefrom, and means 9,23,24,50–57, or 66 responsive to signals from the signal providing means 4,10,14–22 for actuating the material containing means to release a controlled quantity of the material to the adjacent atmosphere.

The signal providing means typically comprises means 4,10,14–22 responsive to a condition in an electronic or optical circuit, such as digital data processing means 10 responsive to a condition in an entertainment device.

Typically the material containing means 5 comprises means for holding a supply of aroma producing fluid 6 in a first compartment 28 thereof and for moving a predetermined quantity of the fluid 6 into a separate second compartment 30,41, or 64 of the containing means 5, and wherein the actuating means 9,23,24,50–57, or 66 comprises means for releasing the moved fluid 6 from the second compartment 30,41, or 64 into the atmosphere and then actuating the holding and moving means to again move a like quantity of fluid from the first compartment 28 to the second compartment 30,41, or 64. The releasing means typically comprises solenoid 9,23 or 50,51 or other electromechanical activating means, such as bipolar switching means, for opening an outlet means 33 or 43 in the second compartment 30 or 41 when actuated by the signal providing means 4,10,14–22 and then closing the outlet means 33 or 43 after a predetermined time.

Typical apparatus comprises also means 3,70, or 80 for directing the released fluid 6 in a predetermined direction, and the directing means 3,70,80 typically is capable of being adjusted by a person using the apparatus to direct the released fluid 6 toward the nose of the person or, selectively, toward a predetermined region in the midst of a small group of (typically fewer than about ten) persons. Some typical apparatus comprises also means such as a fan 13 for subsequently moving the released fluid 6 away from the vicinity of the using person or persons and for moving unscented air into the region occupied by the using person or persons.

In some embodiments of the invention, as in FIG. 9, the releasing means 65,66 typically comprises means 66 for forming a bubble of vapor 67 from the fluid in the second compartment 64 and pushing a droplet 68 in the bubble 67 through an outlet 69 and into the atmosphere. Typically the bubble forming means 65,66 comprises means for heating the adjacent fluid 67 so as to expand the fluid and force a droplet 68 thereof through the outlet 69, and the actuating means 66 typically comprises electrical heating means 65,66 and means responsive to the signal providing means 4,10, 14–22 for furnishing an electric current to the heating means 65,66.

Typical apparatus, as in FIGS. 11 or 12, may comprise also tubular means 70 or 80 for guiding the material 6 released from the containing means 5 to a selected location, the guiding means typically being capable of conveying the released material 6 to, or adjacent to, the nose of a person using the apparatus.

Typical apparatus according to the invention, as in FIGS. 1–4 or 10, for providing aroma emitting material 6 to a predetermined region from time to time may comprise a plurality of apparatuses as summarized above and an enclosure 1 comprising a first compartment below the base 12 of the venting chamber 11 for holding the apparatuses, a second compartment 11 adjacent to, and communicating with, the first compartment, to receive aroma producing material 6 therefrom when at least one of the confining means 5 thereof is actuated to release a quantity of such material, an adjustable directional opening 3 in the second compartment 11 for directing material 6 therefrom toward a selected region beyond the apparatuses, and means such as the fan 13 for blowing air and any aroma producing material 6 therein out from the second compartment 11 through the directional opening 3 toward the selected region.

Such apparatus typically comprises also programmable digital electronic means 4,10,14–22 for providing signals to control the actuating means 8 in the various apparatuses, with the digital signal providing means 4,10,14–22 typically located in the enclosure 1. The apparatus typically comprises also switching means 91 for programming the signal providing means 22 to select the specific aromas, the timing and intensities of the emission thereof, and the blowing speeds applied to the air and aroma producing material in the second compartment 11. The switching means 91 typically is located on an outer surface 4 of the enclosure 1.

While the forms of the invention herein disclosed constitute currently preferred embodiments, many others are possible. It is not intended herein to mention all of the possible equivalent forms or ramifications of the invention. It is to be understood that the terms used herein are merely descriptive rather than limiting, and that various changes may be made without departing from the spirit or scope of the invention.

I claim:

1. Apparatus for providing aroma emitting material to a predetermined region from time to time comprising means for providing signals at selected times when an aroma is to be emitted, means for containing an aroma producing material and confining the material therein except when actuated to release some of the material therefrom, and means responsive to signals from the signal providing means for actuating the material containing means to release a controlled quantity of the material to the adjacent atmosphere;

the material-containing means comprising means for holding a supply of aroma producing fluid in a first compartment thereof and for moving a predetermined quantity of the fluid into a separate second compartment of the containing means;

the actuating means comprising means for releasing the moved fluid from the second compartment into the atmosphere and then actuating the holding and moving means to again move a like quantity of fluid from the first compartment to the second; and the releasing means comprising solenoid means for opening an outlet in the second compartment when actuated by the signal providing means and then closing the outlet after a predetermined time; or comprising means for forming a bubble of vapor from the fluid in the second compartment and pushing the bubble through an outlet and into the atmosphere, the bubble forming means comprising means for heating the fluid in the second compartment so as to expand the fluid and force it through the outlet, and the actuating means comprising electrical heating means and means responsive to the signal providing means for furnishing an electric current to the heating means.

2. Apparatus as in claim 1, wherein the signal providing means comprises means responsive to a condition in an electronic or optical circuit.

3. Apparatus as in claim 2, wherein the electronic or optical circuit comprises means responsive to a condition in an entertainment device.

4. Apparatus as in claim 2, wherein the electronic or optical circuit comprises digital data processing means.

5. Apparatus as in claim 1, comprising also means for directing the released fluid in a predetermined direction.

6. Apparatus as in claim 5, wherein the directing means is constructed and arranged to be adjusted by a person using the apparatus to direct the released fluid toward the nose of the person or, selectively, toward a predetermined region in the midst of a group of fewer than about ten persons.

7. Apparatus as in claim 6, comprising also means for subsequently moving the released fluid away from the vicinity of the using person or persons and for moving unscented air into the region occupied by the using person or persons.

8. Apparatus as in claim 1, comprising also tubular means for guiding the material released from the containing means to a selected location.

9. Apparatus as in claim 8, wherein the guiding means is constructed and arranged to convey the released material to, or adjacent to, the nose of a person using the apparatus.

10. Apparatus for providing aroma emitting material to a predetermined region from time to time comprising a plurality of apparatuses as in claim 1 and an enclosure comprising a first compartment for holding the apparatuses, a second compartment adjacent to, and communicating with, the first compartment, to receive aroma producing material therefrom when at least one of the confining means thereof is actuated to release a quantity of such material, an adjustable directional opening in the second compartment for directing material therefrom toward a selected region beyond the apparatuses, and means for blowing air and any aroma producing material therein out from the second compartment through the directional opening toward the selected region.

11. Apparatus as in claim 10, comprising also programmable digital electronic means for providing signals to control the actuating means in the plurality of apparatuses.

12. Apparatus as in claim 11, wherein the digital signal providing means is located in the enclosure.

13. Apparatus as in claim 11, comprising also switching means for programming the signal providing means to select the specific aromas, the timing and intensities of the emission thereof, and the blowing speeds applied to the air and aroma producing material in the second compartment.

14. Apparatus as in claim 13, wherein the switching means is located on an outer surface of the enclosure.

15. Apparatus as in claim 1 wherein the holding and moving means comprises a sliding cylindrical valve that provides openings through which fluid in the first compartment flows to the second compartment when the valve is in a first end position and through which the fluid in the second compartment flows to the atmosphere when the valve is in a second end position, opposite to the first end position; and the solenoid means comprises electrically actuated means for selectively providing magnetic force to hold the sliding valve at the first end position and, when actuated from time to time by the signal providing means, to move it to the second end position and then back to the first end position.

* * * * *